(12) United States Patent
Ozinsky et al.

(10) Patent No.: US 8,744,164 B2
(45) Date of Patent: Jun. 3, 2014

(54) AUTOMATED ANALYSIS OF IMAGES USING BRIGHT FIELD MICROSCOPY

(75) Inventors: Adrian Ozinsky, Seattle, WA (US); Jyrki Juhani Selinummi, Nokia (FI); Ilya Shmulevich, Seattle, WA (US); Pekka Ruusuvuori, Pori (FI)

(73) Assignee: Institute for Systems Biology, Seattle, WA (US)

( * ) Notice: Subject to any disclaimer, the term of this patent is extended or adjusted under 35 U.S.C. 154(b) by 498 days.

(21) Appl. No.: 13/079,776

(22) Filed: Apr. 4, 2011

(65) Prior Publication Data

US 2011/0254943 A1  Oct. 20, 2011

Related U.S. Application Data

(60) Provisional application No. 61/321,495, filed on Apr. 6, 2010.

(51) Int. Cl.
  *G06K 9/00* (2006.01)
  *H04N 7/18* (2006.01)
(52) U.S. Cl.
  USPC ............................. 382/133; 382/128; 348/79
(58) Field of Classification Search
  USPC ........................................................ 348/79
  See application file for complete search history.

(56) References Cited

U.S. PATENT DOCUMENTS 6,716,588 B2 * 4/2004 Sammak et al. ............... 435/7.2
2012/0013727 A1 * 1/2012 Breniman et al. ............. 348/79

OTHER PUBLICATIONS

Selinummi J, et al. (Oct. 2009) Bright Field Microscopy as an Alternative to Whole Cell Fluorescence in Automated Analysis of Macrophage Images. PLoS ONE 4(10): e7497.
U. Agero et al. "Cell surface fluctuations studied with defocusing microscopy" Physical Review E 67, 051904 2003, (9 pages).
U. Agero et al., "Defocusing Microscopy" Microscopy Research and Technique 65:159-165 (2004).
J. C. Neto et al., "Measuring Optical and Mechanical Properties of a Living Cell with Defocusing Microscopy" Biophysical Journal vol. 91 Aug. 2006 1108-1115.

* cited by examiner

*Primary Examiner* — Chikaodili E Anyikire
(74) *Attorney, Agent, or Firm* — Milstein Zhang & Wu LLC; Joseph B. Milstein

(57) ABSTRACT

A system and method for automatically observing and counting cells without using a stain or a fluorescent material. The system includes an optical microscope having a sensor that provides an electrical signal representative of a field of view. The microscope is motorized so as to allow automatic change of focus. A sample containing cells to be analyzed is provided. No stain or fluorescent substance is used. When the microscope is operated in a deliberately out-of-focus condition, cells appear to have either a bright or a dark spot that can be used to report the number of cells in the sample. The intensity variation detected in images acquired in different focal planes is used to identify cell shapes using image analysis software such as CellProfiler. A result is reported in any convenient format, such as a false color image.

27 Claims, 10 Drawing Sheets

FIG. 2A
FIG. 2B
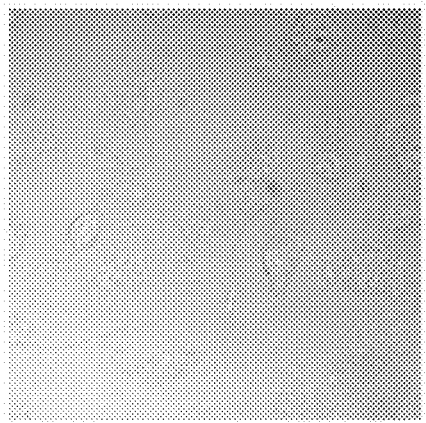
(a)
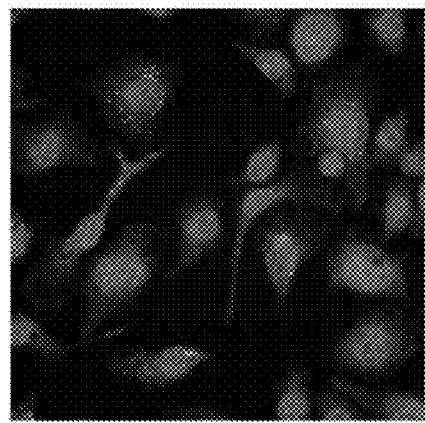
(b)
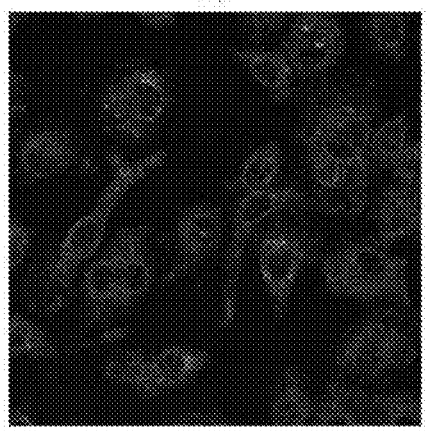
(c)
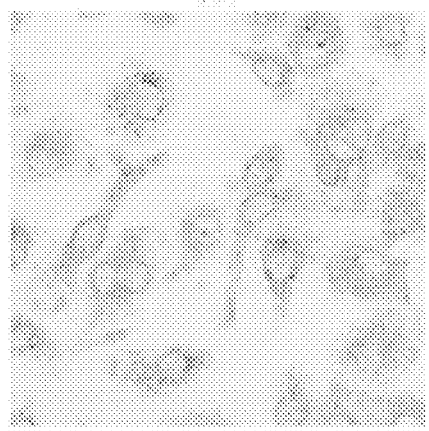
(d)
FIG. 2C
FIG. 2D

AUTOMATED ANALYSIS OF IMAGES USING BRIGHT FIELD MICROSCOPY

STATEMENT REGARDING FEDERALLY FUNDED RESEARCH OR DEVELOPMENT

The U.S. Government has certain rights in this invention pursuant to Grant No. 70NANB8H8117 awarded by the National Institute of Science and Technology, and Grant No. P50 GM076547 awarded by the National Institutes of Health/NIGMS.

CROSS-REFERENCE TO RELATED APPLICATIONS

This application claims priority to and the benefit of co-pending U.S. provisional patent application Ser. No. 61/321,495, filed Apr. 6, 2010, which application is incorporated herein by reference in its entirety.

FIELD OF THE INVENTION

The invention relates to observing cells in optical images in general and particularly to systems and methods in which cells are counted.

BACKGROUND OF THE INVENTION

Cell detection is a fundamental procedure in any biomedical study where microscopy images of cell populations are used. Cell detection can be used for counting the individual cells, or as a basis for further analysis, ranging from feature extraction to single cell tracking. This procedure has been intensively studied in the image processing community.

Fluorescence microscopy is the standard tool for detection and analysis of cellular phenomena. This technique, however, has a number of drawbacks such as the limited number of available fluorescent channels in microscopes, overlapping excitation and emission spectra of the stains, and phototoxicity.

The development of highly specific stains and probes, for example the green fluorescent protein and its derivatives, have made fluorescence microscopy the standard tool for visualization and analysis of cellular functions and phenomena. On the other hand, automated microscopes and advances in digital image analysis have enabled high-throughput studies automating the imaging procedure and cell based measurements. In fluorescence microscopy of eukaryotic cells, automated single-cell quantification can be achieved using multiple fluorescent probes and channels in a single experiment. The first fluorescence channel enables detection of stained nuclei, resulting in markers for cell locations. The second fluorescence channel visualizes the areas occupied by whole cells or cytoplasm, for example by a cytoskeletal actin stain, as described in Moffat J, Grueneberg D A, Yang X, Kim S Y, Kloepfer A M, et al. (2006) A lentiviral RNAi library for human and mouse genes applied to an arrayed viral high-content screen. Cell 124: 1283-1298. Alternatively, a nonspecific subcellular stain can be used for whole cell detection. Regardless of the approach for whole cell staining, cells that are touching or partly overlapping can be automatically separated with the help of the nuclei markers of the first channel, as describe in Carpenter A E, Jones T R, Lamprecht M R, Clarke C, Kang I H, et al. (2006) CellProfiler: image analysis software for identifying and quantifying cell phenotypes. Genome Biol 7: R100. Finally, subcellular phenomena are quantified by measuring different properties of the first and second channels, or by using additional organelle and molecule specific probes and extra fluorescence channels, for example in colocalization measurements, as described in Bolte S, Cordelières F P (2006) A guided tour into subcellular colocalization analysis in light microscopy. J Microsc 224: 213-232.

Because of the limited number of fluorescent channels available, and because of partly overlapping excitation and emission spectra of the probes, studies involving subcellular colocalization are commonly carried out without nuclear or whole cell staining. As a consequence, cell-by-cell measurements are not possible. Single cell measurements are also difficult or even impossible in cells that are used for negative control, where the lack of fluorescence is used for the detection of some phenomena. Furthermore, there are other limitations in fluorescence microscopy, such as phototoxicity and imaging setup complexity. These problems have motivated the search for alternate methods to replace at least some of the fluorescence channels with standard transmitted light microscopy.

A number of problems in counting cells using the conventional methods have been observed. These problems include the contamination of the cells (and possibly the growth culture in which they are found) with extraneous chemical substances that are needed for counting, but that make the further use of the cells impractical or impossible.

There is a need for systems and methods that provide the ability to count cells without subjecting the cells to extraneous chemicals.

SUMMARY OF THE INVENTION

While the invention will be described using a microscope slide having a surface upon which cells to be examined are situated, it is to be understood that the invention can equally well be practiced using other well known substrates for supporting cells, such as plates, objects having wells defined therein, culture dishes, cell growth media, and their equivalents.

In one aspect, the invention features a method of automatically identifying the number of cells present in a sample. The method comprises the steps of providing an optically transparent supporting surface, the optically transparent supporting surface situated for observation in an optical microscope having a sensor sensitive to optical illumination, the sensor having an output terminal configured to provide as output a signal representative of a field of view monitored by the sensor; providing a sample comprising at least one cell situated on the optically transparent supporting surface; deliberately operating the optical microscope in bright field mode with optical illumination so as to focus at one or more different focal planes situated along a direction normal to the optically transparent supporting surface, so that the at least one cell is within the field of view of the sensor; observing with the sensor an image selected from the group of images consisting of one or more bright spots and one or more dark spots, the image corresponding to a specific focal condition; providing from the output terminal of the sensor an output signal representative of the image; processing the output signal representative of the image to compute a number of bright spots or a number of dark spots; and reporting the number of bright spots or the number of dark spots as the number of cells present in the sample.

In some embodiments, the sample comprising at least one cell is free of a staining agent. In some embodiments, the sample comprising at least one cell is free of a fluorescent agent. In some embodiments, the method of automatically identifying the number of cells present in a sample further comprises the step of having a human operator view an image observed by the sensor.

In some embodiments, the step of processing the output signal representative of the image is performed in a computer-based analyzer. In some embodiments, the computer based-analyzer provides a synthetic image of the sample comprising at least one cell, the synthetic image including an outline of the at least one cell in false color. In some embodiments, the method of automatically identifying the number of cells present in a sample further comprises the step of focusing on the at least one cell, the step of focusing on the at least one cell being performed prior to the step of observing with the sensor an image selected from the group of images consisting of one or more bright spots and one or more dark spots.

In some embodiments, the specific focal condition is an out-of-focus condition.

In another aspect, the invention relates to an automated image processing system. The system comprises an optical microscope having a sensor sensitive to optical illumination, the sensor having an output terminal configured to provide as output a signal representative of a field of view monitored by the sensor, the optical microscope configured to allow operation of the optical microscope in bright field mode with optical illumination and configured to allow the optical microscope to change focus along a direction normal to an optically transparent supporting surface situated for observation in the optical microscope so as deliberately to attain at least one image along the direction normal to the optically transparent supporting surface of a sample situated within the field of view of the optical microscope; a computer-based image processor configured to receive the output signal representative of a field of view monitored by the sensor from the sensor, the image processor configured to identify one or more images out of the at least one image, the image processor configured to analyze the at least one image to deduce a property of the sample from the one or more images; and a reporting apparatus in communication with the computer-based image processor, the reporting apparatus configured to provide a report of the property of the sample.

In some embodiments, the at least one image is an image selected from the group of images consisting of one or more bright spots and one or more dark spots; the image processor is configured to compute a number of bright spots or a number of dark spots in the image; and the property reported by the reporting apparatus is the number of bright spots or the number of dark spots, so that the property reported is a number of cells present in a sample situated on a portion of the optically transparent supporting surface that is situated within the field of view of the optical microscope. In some embodiments, the automated image processing system further comprises an actuator configured to change a focal condition of the optical microscope. In some embodiments, the automated image processing system further comprises a computer-based control apparatus configured to control the focal condition of the optical microscope by driving the actuator.

In some embodiments, the computer-based control apparatus configured to control the focal condition of the optical microscope is configured to operate to focus at one or more different focal planes situated along the normal to the optically transparent supporting surface on one or more cells in the field of view. In some embodiments, the automated image processing system further comprises an actuator configured to change a lens so as to change a magnification or a dimension of a field of view of the optical microscope.

In some embodiments, the reporting apparatus provides a synthetic image. In some embodiments, the synthetic image includes false color. In some embodiments, the reporting apparatus provides a report that is recorded for later use. In some embodiments, the reporting apparatus provides a report that is displayed to a user. In some embodiments, the optical microscope is configured to allow simultaneous mounting of the sensor and an eyepiece suitable for a human operator. In some embodiments, the automated image processing system further comprises one or more power supplies to operate the optical microscope, the computer-based image processor, and the reporting apparatus.

In some embodiments, the at least one image is selected from a bright field z-stack of images along a z-dimension; the image processor is configured to compute a variation with respect to the z-dimension of the intensity values within the x,y plane between a first image and a second image of the bright field z-stack, to construct a two-dimensional projection image of increased contrast, and to deduce from the two-dimensional projection image of increased contrast a feature of at least one cell of the sample; and the reporting apparatus is configured to report the feature of the at least one cell present in the sample. In some embodiments, the property is a border of the at least one cell. In some embodiments, the system is configured to spatially distinguish at least one cell from another cell within the sample In yet another aspect, the invention features a method of automatically identifying a feature of a cell present in a sample. The method comprises the steps of: providing an optically transparent supporting surface, the optically transparent supporting surface situated for observation in an optical microscope having a sensor sensitive to optical illumination, the sensor having an output terminal configured to provide as output a signal representative of a field of view monitored by the sensor; providing a sample comprising at least one cell situated on the optically transparent supporting surface; deliberately operating the optical microscope in bright field mode with optical illumination so as to focus at one or more different focal planes situated along a direction normal to the optically transparent supporting surface to form a bright field z-stack of images along a z-dimension, so that the at least one cell is within the field of view of the sensor; observing with the sensor a plurality of images selected from the bright field z-stack; providing from the output terminal of the sensor an output signal representative of the plurality of images; processing for at least two of the plurality of images the output signal representative of the plurality of images to obtain intensity values of pixels within an x,y plane; measuring a variation with respect to the z-dimension of the intensity values within the x,y plane between a first image and a second image of the at least two of the plurality of images; constructing a two-dimensional projection image of increased contrast; deducing from the two-dimensional projection image of increased contrast a feature of the at least one cell; and reporting the feature of the at least one cell present in the sample.

In some embodiments, the feature is an observable property of the at least one cell. In some embodiments, the observable property is a border of the at least one cell. In some embodiments, the at least one cell is spatially distinguished from another cell within the sample.

In some embodiments, images are acquired at several focus levels forming a bright field z-stack, and by measuring the intensity variations of this stack over the z-dimension, a new two dimensional projection image of increased contrast is constructed and analyzed. In one embodiment, with additional information for locations of each cell, such as stained nuclei, this bright field projection image can be used instead of whole cell fluorescence to locate borders of individual cells, separating touching cells, and enabling single cell analysis. In another embodiment, no staining is required.

The foregoing and other objects, aspects, features, and advantages of the invention will become more apparent from the following description and from the claims.

BRIEF DESCRIPTION OF THE DRAWINGS

The objects and features of the invention can be better understood with reference to the drawings described below, and the claims. The drawings are not necessarily to scale, emphasis instead generally being placed upon illustrating the principles of the invention. In the drawings, like numerals are used to indicate like parts throughout the various views.

FIG. 2 is a diagram that illustrates contrast enhancement by standard deviation projection of bright field image stack.

FIG. 2A is a low contrast bright field image.

FIG. 2B is an image that illustrates the use of fluorescence staining for whole cell detection.

FIG. 2C is a standard deviation projection of stack of bright field images, for which no fluorescence is required.

FIG. 2D is an inverse of the projection for another visualization of the projection result in FIG. 2C. In addition to increased contrast, the projection (FIG. 2C and FIG. 2D) also suppress background nonuniformities visible in FIG. 2A.

FIG. 3 is a diagram that illustrates whole cell segmentation using different input data, in which all the illustrated methods require the use of fluorescent nuclei as markers for each cell.

FIG. 4 is a diagram showing the pixel-by-pixel comparison of whole cell segmentation using bright field projections against fluorescence ground truth.

DETAILED DESCRIPTION

Figure 1:
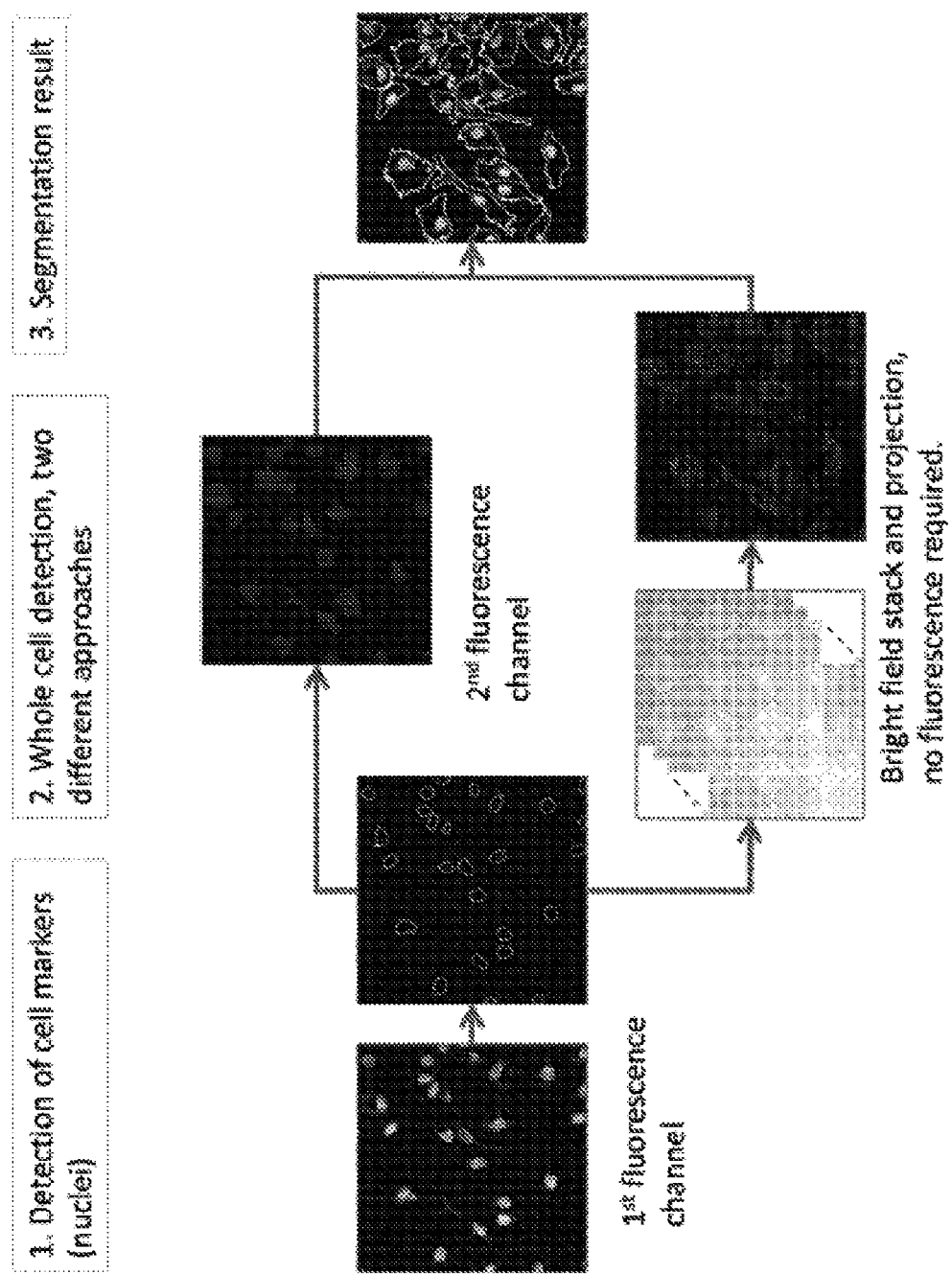
FIG. 1 is a flowchart of the cell segmentation procedure in which whole cell fluorescent staining is replaced by projection images calculated from bright field image stacks of different focal planes.

This invention relates to counting and identifying cells using transmitted light optical microscopy illuminated with visible light. In some embodiments, images are acquired using variants of transmitted light microscopy, including bright field, phase contrast, differential interference contrast (DIC)/Nomarski interference contrast, dark field, Hoffman modulation, variable relief optics, and polarization optics.

As used in this application, the terms "bright field microscopy," "phase contrast microscopy," "differential interference contrast (DIC) microscopy," "dark field microscopy," and "cross-polarized light microscopy" have the meanings given hereinbelow.

Bright field microscopy is an optical microscopy illumination technique in which contrast in the sample is caused by absorbance of some of the transmitted light in dense areas of the sample.

Phase contrast microscopy is an optical microscopy illumination technique in which contrast in the sample is caused by interference of small phase shifts due to different path lengths for the light passing through the sample.

Differential interference contrast microscopy (DIC) is an optical microscopy illumination technique in which contrast in the sample is caused by interference between two orthogonally polarized illumination paths.

Dark field microscopy is an optical microscopy illumination technique in which contrast in the sample is caused by light scattered by the sample.

Cross-polarized light microscopy is an optical microscopy illumination technique in which contrast in the sample is caused by rotation of polarized light through the sample.

We describe a method to automatically detect cell population outlines directly from bright field images, including a method that relies on using stacks of brightfield images where the same sample has been imaged successively in different planes of focus, including planes of focus beyond the plane of the object and planes focused at different planes within the volume of the object.

By imaging samples with several focus levels forming a bright field z-stack, and by measuring the intensity variations of this stack over the z-dimension, we construct a new two dimensional projection image of increased contrast. In one embodiment, with additional information for locations of each cell, such as stained nuclei, this bright field projection image can be used instead of whole cell fluorescence to locate borders of individual cells, separating touching cells, and enabling single cell analysis. In another embodiment, no staining is required. Using the popular CellProfiler freeware cell image analysis software mainly targeted for fluorescence microscopy, we demonstrate the validity of our method by automatically segmenting low contrast and rather complex shaped murine macrophage cells.

The approach frees up a fluorescence channel, which can be used for subcellular studies. It also facilitates cell shape measurement in experiments where whole cell fluorescent staining is either not available, or is dependent on a particular experimental condition. We show that whole cell area detection results using our projected bright field images match closely to the standard approach where cell areas are localized using fluorescence, and conclude that the high contrast bright field projection image can directly replace one fluorescent channel in whole cell quantification. MATLAB code for calculating the projections is provided in Appendix A.

The bright field channel, although readily available in all microscopes (including both monocular and binocular microscopes), is often neglected in cell population studies. Firstly, the cells are often nearly transparent, making the contrast very poor. Even by manual visual cell analysis it is often impossible to reliably detect the locations of cell borders, especially if the cells are clumped together. Furthermore, since no specific staining is applied, subcellular phenomena cannot be detected and nuclei are often only faintly visible. Recently, however, a number of studies have been published showing the usefulness of the bright field channel in cell detection and automated image analysis of cell populations. In Quantitative Phase Microscopy, a phase map of samples is estimated from bright field images of different focus levels, as described in Curl C L, Bellair C J, Harris T, Allman B E, Harris P J, et al. (2005) Refractive index measurement in viable cells using quantitative phase-amplitude microscopy and confocal microscopy. Cytometry A 65: 88-92, using proprietary software to greatly increase the contrast. In Ali R, Gooding M, Christlieb M, Brady M (2008) Advanced phase-based segmentation of multiple cells from brightfield microscopy images; Proc. 5th IEEE International Symposium on Biomedical Imaging From Nano to Macro ISBI 2008; pp. 181-184, a similar approach was taken, but the phase map was measured using lowpass digital filtering, followed by a computationally expensive level set based segmentation of individual cells. Texture analysis methods have also been used for bright field cell detection, such as the method presented by Korzynska A, Strojny W, Hoppe A, Wertheim D, Hoser P (2007) Segmentation of microscope images of living cells, Pattern Anal Appl 10: 301-319, where cell contours were extracted after initial segmentation. For round cells with rather good contrast borders, such as yeast, there are multiple algorithms available. See for example, Niemistö A, Korpelainen T, Saleem R, Yli-Harja O, Aitchison J, et al., (2007) A K-means segmentation method for finding 2-D object areas based on 3-D image stacks obtained by confocal microscopy, Proc. 29th Annual International Conference of the IEEE Engineering in Medicine and Biology Society EMBS 2007. pp. 5559-5562; Gordon A, Colman-Lerner A, Chin T E, Benjamin K R, Yu R C, et al., (2007) Single-cell quantification of molecules and rates using open-source microscope-based cytometry, Nat Methods 4: 175-181, and Kvarnström M, Logg K, Diez A, Bodvard K, Käll M (2008) Image analysis algorithms for cell contour recognition in budding yeast, Opt Express 16: 12943-12957.

In cell tracking, the bright field cell segmentation is often presented as a preprocessing step followed by the actual tracking algorithm, as described in Zimmer C, Zhang B, Dufour A, Thebaud A, Berlemont S, et al., (2006) On the digital trail of mobile cells, IEEE Signal Proc Mag 23: 54-62. Utilizing bright field images with rather good contrast, it has also been shown that it is possible to classify between different cell types without fluorescent stains, as described in Long X, Cleveland W L, Yao Y L (2008) Multiclass cell detection in bright field images of cell mixtures with ECOC probability estimation, Image Vision Comput 26: 578-591. Finally, special microscopy techniques such as digital holography, described in Mölder A, Sebesta M, Gustafsson M, Gisselson L, Wingren A G, et al. (2008) Non-invasive, label-free cell counting and quantitative analysis of adherent cells using digital holography, J Microsc 232: 240-247, have been used instead of fluorescent staining.

In the present approach the cells are imaged with several different focal planes as in Curl and Ali, but instead of solving for the phase map, we measure the intensity variations in the z-dimension of bright field stack, creating a new 2-D image for analysis. The pixel intensities inside the cells vary when the focus is changing, but the background intensity stays more constant throughout the stack, resulting in relatively high variation inside the cells, but almost zero outside. Therefore, in the resulting projections the cells appear as brighter objects on an essentially black background, enabling us to replace the fluorescence image of whole cell staining with this bright field projection. In another embodiment, the cells appear as dark spots on a brighter background. In comparison to the previous bright field based cell segmentation techniques presented in the literature, this approach is more straightforward to implement, and the resulting bright field projection image is directly applicable for segmentation using CellProfiler analysis software designed for fluorescent microscopy. Furthermore, with the exception of a preprocessing step with image filtering, no parameters need to be set when calculating the projection. As validation, we apply the technique for segmentation of mouse bone marrow derived macrophage cells with complex shapes and very low contrast.

The resulting projections are shown to enable whole cell segmentation if only nuclear staining or other marker, such as manual cell marking for each cell is available, removing the need for an additional fluorescent channel for whole cell detection.

Methods

To evaluate the performance of projection based methods, we acquired test image data by culturing and imaging bone marrow macrophages (BMM). The macrophages isolated from BL6 were cultured on glass cover slip in RPMI medium, supplemented with 10% fetal bovine serum, 100 u/ml penicillin, 100 μg/ml streptomycin, 2 mM GlutaMAX and 50 ng/ml m-CSF (37 C, 5% CO2). The cells were stimulated with LPS 100 ng/ml for 1, 2, 4, 6, 18, and 24 hours, fixed with 3% Paraformaldehyde for 20 min and stained with BODIPY 493/503 (Invitrogen) for lipid bodies, and Sytox (Invitrogen) for nuclei. Unstimulated macrophages as well as the stimulated cells of different time points were imaged with Leica DMIRB confocal laser scanning microscope.

The image stacks form eight groups with varying cell morphologies: two image sets of unstimulated macrophage cells, and a time series experiment with six groups of macrophage images from different time points during the stimulation. For each group, there are five image stacks, each consisting of three channels: 1. fluorescent nuclei 2. fluorescence subcellular stain for lipid bodies also visualizing the cytoplasm and 3. bright field channel. Each of the stacks for every channel comprise 20 individual z-slices. One stack for each channel of the time point 18 h had to be removed because it was erroneously imaged as a single slice instead of a stack. In total, the test data set includes nearly 800 cells.

To enable whole cell segmentation from bright field images, the contrast must be enhanced by increasing the intensity differences between cell and background areas. We achieve this by calculating different measures of variation in the z-direction, projecting the bright field stacks into two dimensional (2-D) images. That is, each pixel in the resulting 2-D projections corresponds to a measure of intensity variation in the z-direction in the original stack in that specific x,y pixel location. Since there is typically less z-intensity variation in the background than in cells, these two classes of pixels can be separated. Specifically, we make the projections using standard deviation (STD), interquartile range (IQR), coefficient of variation (CV), and median absolute deviation (MAD) measures.

The STD projection image is constructed by calculating the standard deviation of intensities in the z-direction for each pixel of the original stack:

$$\sigma = \sqrt{\frac{1}{N-1} \sum_{i=1}^{N} (I_i - \mu)^2} \,, \quad \text{Eqn. (1)}$$

where $I_i$ is the pixel intensity of z-slice i, $\mu$ is the mean of the pixel intensities, and N is the total number of z-slices.

For a more robust measure of variation we calculated IQR projection, the difference between the 75th and the 25th percentiles of the sample. That is, the lowest 25% and highest 25% of the values are first discarded, and the IQR is the range between the maximum and minimum of all the remaining intensities of z-slices.

In CV projection, the standard deviation of the z-values is divided by the mean of the values $$CV = \sigma/\mu \quad \text{Eqn. (2)}$$

MAD measures how much "on average" one value deviates from the median of all the values, that is, the median deviation from the median of the intensities of all the z-slices for every x,y pixel location:

$$MAD = \text{median}(J) \quad \text{Eqn. (3)}$$

where $I=\{I_i\}_{i=1 \ldots N}$, $\Theta=\text{median}(I)$, and $J=\{|I_i-\Theta|\}$.

To assess the projections' sensitivity to the number of z-slices imaged for each stack, we applied the STD projection to two different types of reduced stacks, consisting only of three slices. First, the three slices were selected by hand representing nearly the whole z-range of the original stack (slices 2, 10 and 19), referred to hereinafter as the 3Slices-method. In another embodiment, we created five reduced versions of the original stacks by selecting the three slices randomly, referred to hereinafter as 3SlicesRandom1 to 3SlicesRandom5.

The automated image analysis and cell segmentation for the evaluation of the various projection methods was carried out by the open source CellProfiler software package, originally designed for fluorescence microscopy. In one embodiment, markers for each cell were obtained by detecting fluorescent nuclei with IdentifyPrimAutomatic analysis module. To smooth out small unwanted details from the projections, a Gaussian lowpass filter radius of 5 pixels was applied by SmoothOrEnhance module. We used the propagation algorithm described in Jones T, Carpenter A, Golland P (2005) Voronoi-based segmentation of cells on image manifolds, Lect Notes in Comput Sc 3765: 535-543 in the Identify Secondary Automatic module for detecting the whole cell areas. For ground truth, the whole cell areas were segmented with the same procedure (excluding the lowpass filter) using fluorescent cytoplasm images to be compared against cell area detection using the various 2-D projections. To simulate a situation where no fluorescent staining is available, the cytoplasmic areas were estimated by an annulus of radius 30 pixels around each nuclei as described, for example, in Schlumberger M C, Käppeli R, Wetter M, Müller A J, Misselwitz B, et al., (2007) Two newly identified SipA domains (F1, F2) steer effector protein localization and contribute to Salmonella host cell manipulation, Mol Microbiol 65: 741-760. This estimation approach is referred to as the Annulus-method.

For further validation, we also enumerated fluorescent spots visible in the second fluorescent channel of the stacks. The spot enumeration was done with a kernel density estimation based algorithm described in Chen T B, Lu H H, Lee Y S, Lan H J (2008) Segmentation of cDNA microarray images by kernel density estimation, J Biomed Inform 41: 1021-1027 using a Gaussian kernel. Since this spot enumeration module is not included in the standard CellProfiler distribution, we implemented the analysis pipeline in the Developer's Version of CellProfiler, running on MATLAB 2008a (MATLAB 7.6) (available from The Math Works, Inc. 3 Apple Hill Drive, Natick, Mass. 01760-2098, USA, http://www.mathworks.com/). The various approaches for whole cell segmentation are summarized in Table 1.

TABLE 1

| Description of Whole Cell Segmentation Method | Abbreviation |
| --- | --- |
| Standard deviation projection | STD |
| Interquartile range projection | IQR |
| Coefficient of variation projection | CV |
| Median absolute deviation projection | MAD |
| Standard deviation projection for a reduced z-stack with three z-slices (2, 10, and 19) out of 20 in original stacks | 3Slices |
| Standard deviation projection for a reduced z-stack with three randomly selected z-slices; Five separate samples | 3SlicesRandom1-5 |
| Whole cell are estimated to extend 30 pixels around the nucleus | Annulus |
| Ground truth fluorescence segmentation using cytoplasm staining | Fluorescence |

We did not discard cells touching image borders, although it is a procedure commonly performed to minimize bias in measurements caused by cells that are only partly visible. These cells allow us to compare segmentation accuracy also on image borders where image quality is often compromised due to nonuniform background. The computational complexity of the analysis is relatively low, taking around 4 seconds per method to calculate the projection and segment the image on a 2 GHz personal computer (PC) running the Windows Vista operating system.

We projected stacks of bright field images into 2-D by various measures of stack z-variation, with the aim of replacing whole cell fluorescent staining. This procedure is outlined in FIG. 1, where markers for each cell are detected from fluorescence, or marked by hand, with two alternative methods for whole cell detection: fluorescence and the projections. FIG. 2 illustrates the contrast improvement by one of the projection approaches (STD). FIG. 2A shows one slice of the original bright field image, while fluorescence staining, the proposed STD projection, and the inverse of the projection are presented in FIG. 2B, FIG. 2C and FIG. 2D, respectively. The difference in contrast between the projection shown in FIG. 2C and the original bright field data shown in FIG. 2A is easily noticeable. Furthermore, since the deviation in background intensities is similar in all the z-slices, the nonuniform background is efficiently removed by the projection.

Figure 3A:
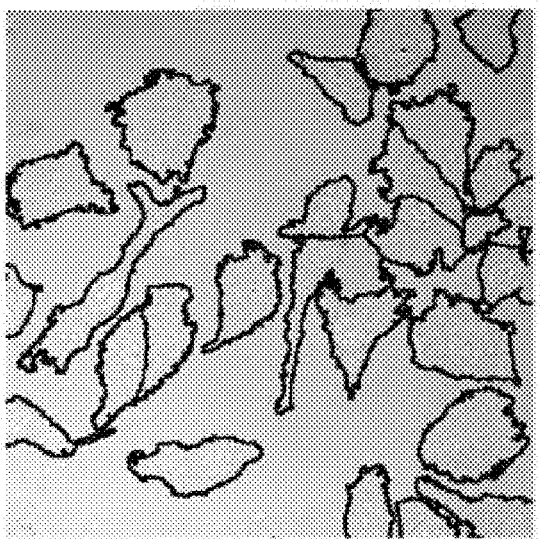
FIG. 3A is an image that illustrates fluorescent whole cell staining.
Figure 3B:
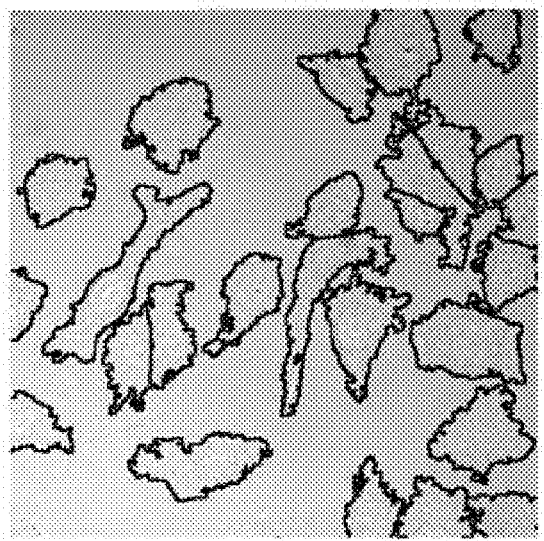
FIG. 3B is an image that illustrates standard deviation projection of a bright field stack.

For assessing the performance of the projection method, we compared automated image segmentation of whole cell areas of fluorescently stained cells to the bright field projections, and to the Annulus-method where the cytoplasm areas were estimated by annuli around the detected nuclei. We were unable to detect the cells of our whole dataset using the best previously published method in the literature for segmenting complex cell shapes in bright field images. FIG. 3 illustrates one segmentation comparison, after image analysis by CellProfiler software. FIG. 3A presents the whole cell segmentation result using fluorescence (FIG. 2B), and in FIG. 3B the whole cell areas were detected from the projected bright field stack (FIG. 2C).

To quantify the segmentation accuracy for all the image stacks of the time series experiment, we measured the precision, represented by $$\text{Precision} = \frac{tp}{tp + fp}, \quad \text{Eqn. (4)}$$

and Recall, represented by $$\text{Recall} = \frac{tp}{tp + fn}, \quad \text{Eqn. (5)}$$

where tp, fp, and fn are the numbers of detected true positive, false positive, and false negative pixels, respectively. Perfect precision would indicate that all the pixels detected by the method under testing (different bright field projections) are also present in the ground truth segmentation result (fluorescence). Perfect recall, on the other hand, would indicate that that no pixels of the fluorescence image are missed by using the bright field projection image.

For a more compact representation of the segmentation accuracy we computed the F-score, represented by:

$$Fscore = \frac{2(\text{Precision} \cdot \text{Recall})}{(\text{Precision} + \text{Recall})}, \quad \text{Eqn. (6)}$$

that is, the harmonic mean of precision and recall. An F-score of 1 corresponds to perfect segmentation accuracy, in which Precision=Recall=1, and there are only true positive and no false positive or false negative observations.

Figure 4A:
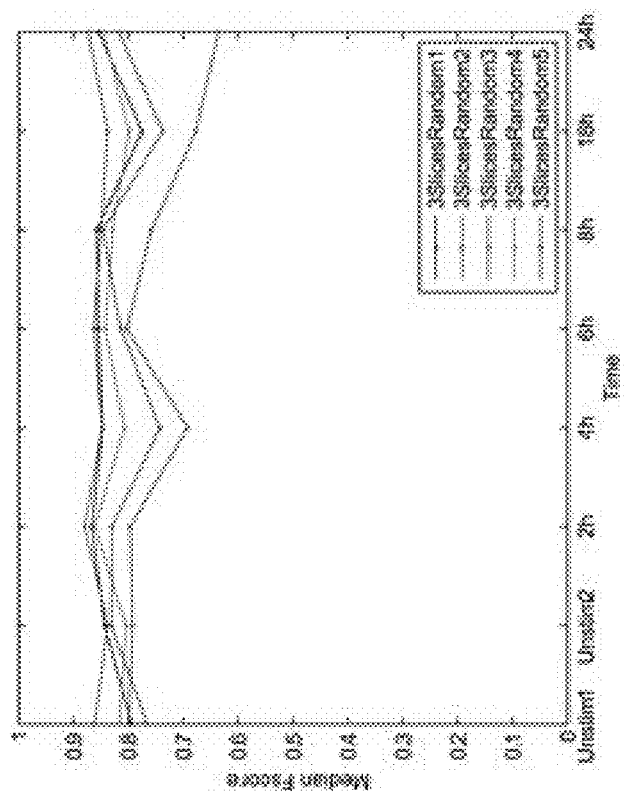
FIG. 4A is a graph showing median F-scores over all cells for each image group, with all the projection methods.
Figure 4B:
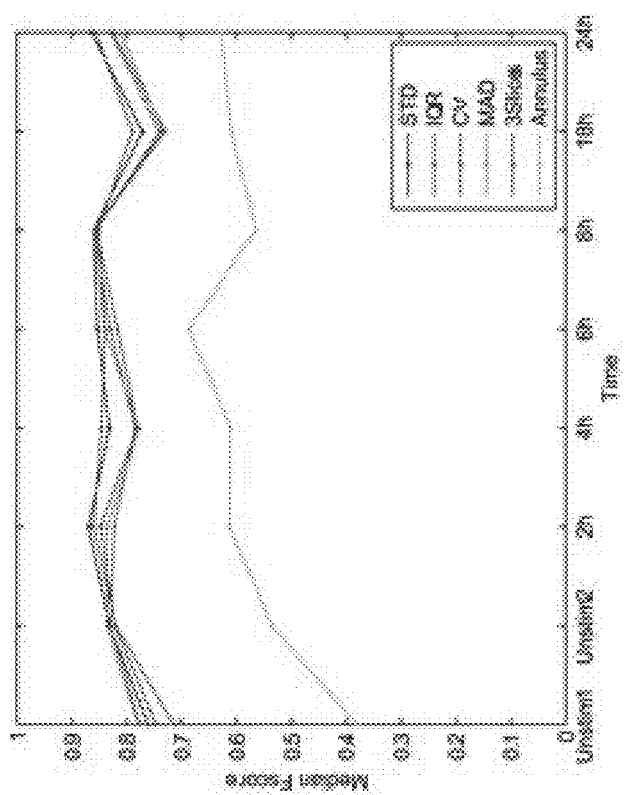
FIG. 4B is a graph showing median F-scores for cell segmentation using standard deviation projection images, each projected from three randomly selected slices.

FIG. 4A presents the per cell segmentation F-score medians over all cells for all the different projection methods against the fluorescence ground truth. Furthermore, the segmentation results for the STD projection of the 3Slices set with only 3 handpicked z-slices are given, as well as the F-score for the Annulus method. FIG. 4B gives the segmentation results of STD projection for 3SlicesRandom1 to 5, assessing the effect of random z-slice selection from the stack for the projection.

With our data set consisting of nearly 800 macrophage cells with highly complex morphologies, the overall performance of the projection methods were close to the ground truth fluorescence staining with the median F-score fluctuating around 0.8. As expected, the F-score is consistently lower for the Annulus method. Boxplots show a number of outliers for each of the eight groups, for all the projection methods. In comparison to the whole dataset, the number of outliers is limited, and the effect of these outliers can be reduced, for example, by discarding the corresponding cells from further analysis, similarly as cells that are too clumped together often need to be removed from automated segmentation results. As seen from the segmentation result images the outliers were caused by segmentation errors overestimating the whole cell areas, suggesting the area of the cell to be a suitable feature for discarding these outliers if necessary.

To evaluate whether the outliers and other variations in the cell segmentation results affect the biological conclusions drawn from the data, we compared subcellular spot counts on a single cell level. By utilizing the second fluorescent channel where lipid bodies are emphasized as bright spots, we first detected the spots in the images (spot detection results for all images available in the supplement site). Then, based on the whole cell segmentation by all the projection approaches, we determined the cell to which each spot belongs. Finally, we discarded the spots outside the detected cells. This procedure enables us to estimate the effect of the different whole cell detection methods on the actual biological conclusions (spot counts per cell), since if the whole cell area detection differs dramatically from the fluorescence ground truth cell area, the numbers of spots detected in these erroneously segmented cells also change. If there is no change in spot counts, the whole cell detection is considered to have worked satisfactorily.

With all the projection methods the spot count per cell increases over time, as previously reported in the literature.

Since each spot was assigned to a specific cell, we also compared the spot per cell counts for each individual cell for further validation. The results of the spot-per-cell analysis are summarized in Table 2 listing the spot count slopes and biases for the different methods against ground truth. All the regression results except Annulus and the STD projection of 3SlicesRandom3 show a near perfect match between cell-by-cell spot counts by projections and fluorescence segmentation. The spots are detected from the fluorescence channel, but are distributed among individual cells by whole cell detection based on the different methods.

TABLE 2

Slopes and biases of spot per cell counts for all methods.

| Segmentation Method | Bias | Slope |
| --- | --- | --- |
| STD | 0.0524 | 0.9616 |
| IQR | 0.0130 | 0.9228 |
| CV | 0.1131 | 0.9656 |
| MAD | −0.0135 | 0.9143 |
| 3Slices | −0.0068 | 0.9520 |
| Annulus | 0.1088 | 0.8467 |
| 3SlicesRandom1 | 0.0358 | 0.9584 |
| 3SlicesRandom2 | 0.0871 | 0.9797 |
| 3SlicesRandom3 | −0.1181 | 0.8130 |
| 3SlicesRandom4 | 0.0773 | 0.9894 |
| 3SlicesRandom5 | 0.0256 | 0.9293 |

EXAMPLES

Contrast Enhancement and Whole Cell Detection with Bright Field 3-D Stack Projections FIG. 5 shows examples of the use of bright field microscopy using projections along the z axis, e.g., perpendicular to the field of view. FIG. 5A is an original bright field image. FIG. 5B is a contrast enhanced projection using bright field z-stacks (no fluorescence) of the field shown in FIG. 5A. FIG. 5C is an automated cell segmentation result. Fluorescence nuclei are used as markers for each cell, and whole cell areas detected using the contrast enhanced bright field images.

Figure 5C:
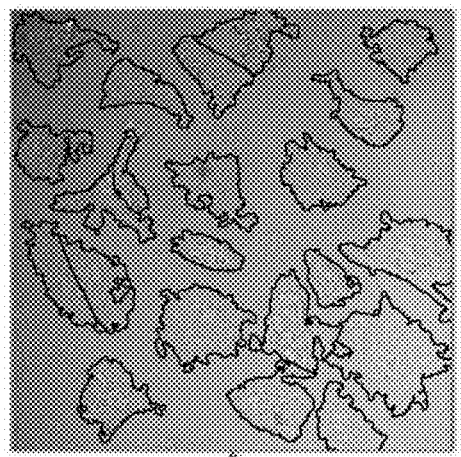
FIG. 5C is an automated cell segmentation result. Fluorescence nuclei are used as markers for each cell, and whole cell areas detected using the contrast enhanced bright field images.
Figure 5F:
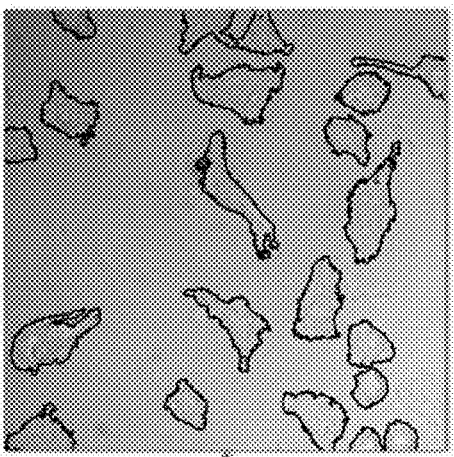
FIG. 5F is an automated cell segmentation result. Fluorescence nuclei are used as markers for each cell, and whole cell areas detected using the contrast enhanced bright field images.
Figure 5B:
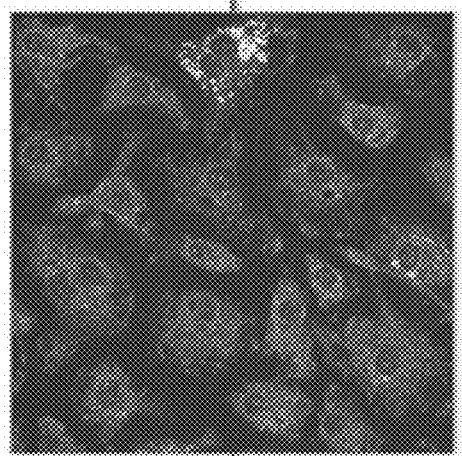
FIG. 5B is a contrast enhanced projection using bright field z-stacks (no fluorescence).
Figure 5E:
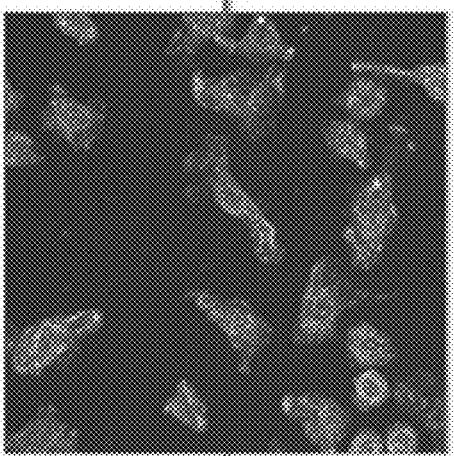
FIG. 5E is a contrast enhanced projection using bright field z-stacks (no fluorescence).
Figure 5A:
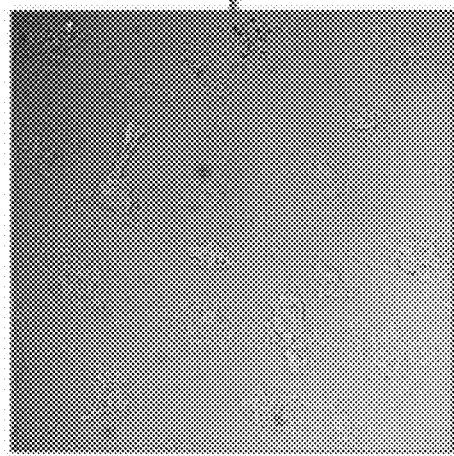
FIG. 5A is an original bright field image.
Figure 5D:
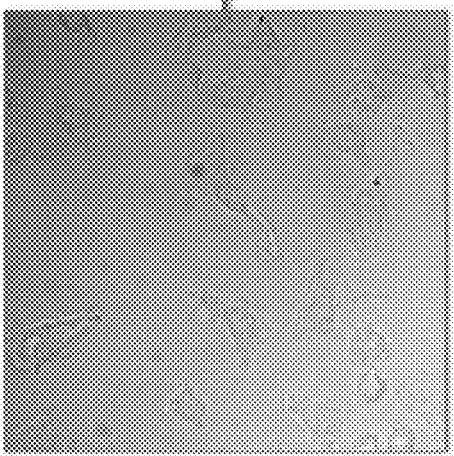
FIG. 5D is another original bright field image.

FIG. 5D is another original bright field image. FIG. 5E is a contrast enhanced projection using bright field z-stacks (no fluorescence) of the field shown in FIG. 5D. FIG. 5F is an automated cell segmentation result. Fluorescence nuclei are used as markers for each cell, and whole cell areas detected using the contrast enhanced bright field images.

We have discussed different z-projection methods for contrast enhancement in bright field image stacks, and shown that the projection approach can replace whole cell fluorescent staining for our set of macrophage images. In single cell detection and segmentation, our method has several advantages over the previously presented bright field based techniques. Firstly, the projection images can be directly used for whole cell segmentation in the freeware CellProfiler software or other tools. Secondly, among the different projection methods tested, the standard deviation projection is computationally very light and trivial to implement, requires no parameters to be set, and still offers excellent segmentation performance. Thirdly, we have successfully applied the whole cell detection method to macrophages, a cell type of high morphological complexity with various protrusions and low contrast. Fourthly, the segmentation results with randomly selected z-slices suggest that precise focusing is not critical. And finally, background intensity variations have no effect on the resulting projection images. The drawback of our approach is the need for taking three images instead of one, requiring a rather fast stage in live cell imaging to acquire the images without cell movement, and currently the segmentation results include outliers resulting from erroneous whole cell detection. Space requirements, on the other hand, are not increased since only the projection images must be stored for analysis.

In the material that we have published on Oct. 22, 2009, we only used images of one cell type, with low contrast all around the cells, without clearly visible cell borders. Halo effects, present in bright field images of many other cell types, for example yeast, might be emphasized erroneously in the projections. Furthermore, it would be interesting to study the segmentation performance with various cell densities and different imaging setups, and to search for optimal conditions for the imaging and subsequent analysis. Many different approaches could also be tested for preprocessing; in this work the standard Gaussian filter was found adequate, but no rigorous parameter optimization or method comparisons were performed.

To fully automate the bright field cell segmentation, the markers for each cell need to be located without fluorescent nuclei, but to the best of our knowledge, there are no robust bright field based methods presented in the literature. The markers could also be set manually, but especially in high throughput studies a manual approach is not realistic. In certain studies where the cells have a very distinctive shape, such as bacteria or yeast cells, the object separation could be done based on cell shape, removing the need for a nuclear marker and thus, the need for fluorescence altogether.

Bright field images are not the only stacks where the standard deviation or other projections should be studied in more detail. In fluorescence microscopy, the studied phenomenon is often visible as subcellular spots, the intensities varying according to the z-levels. This suggests that the spots may be better visible in the standard deviation projections as compared to the methods commonly used, such as mean and maximum projections. The projection approach is also not limited to cellular objects, and any nearly transparent targets should benefit from the increased contrast without the need for any special optics.

FIG. 6 is an additional example showing how bright field microscopy, without the use of fluorescence, can be used to identify individual cells of four different types, and how the cells can be counted automatically.

Figure 6A:
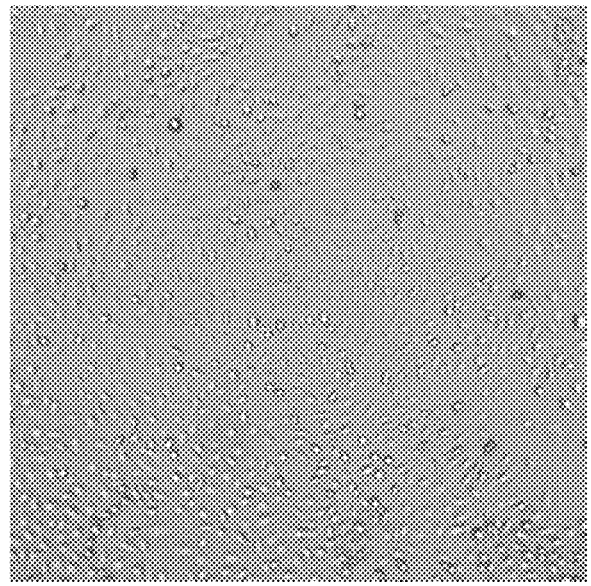
FIG. 6A shows a bright field image of cells that are in focus, for which no fluorescence is required.
Figure 6B:
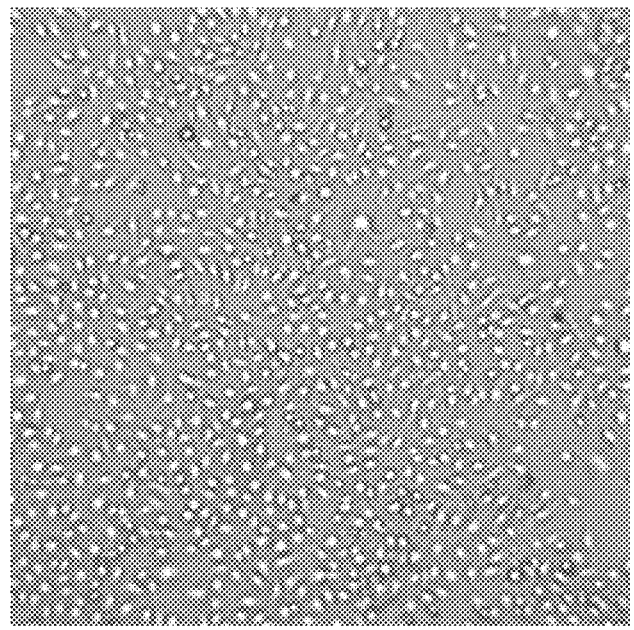
FIG. 6B shows a bright field image of the third type of cells that are out of focus, and which exhibit brighter spots.
Figure 6C:
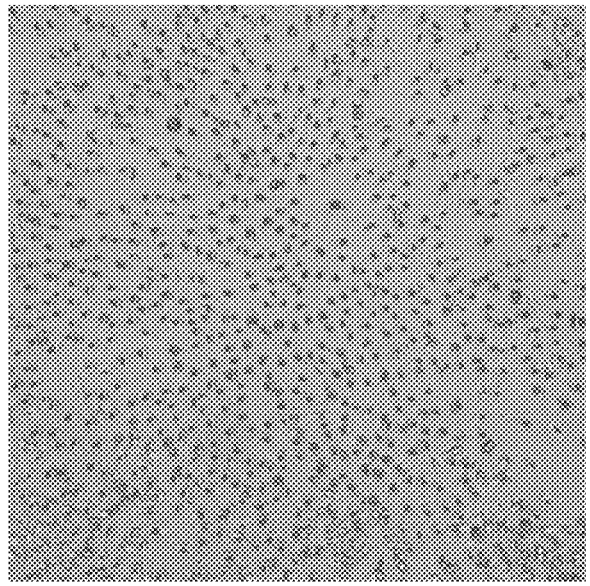
FIG. 6C is an image in which the third type of cells are identified by a thresholding algorithm, and which are shown in false color.

FIG. 6 comprises three images. In a first image, FIG. 6A, a standard bright field optical image taken under conditions of good focus is illustrated, which shows the low contrast difference that is exhibited between cells and a background when a field of cells that have not been treated in any way. In a second image, FIG. 6B, a defocused image is presented, in which each cell is observed to be identifiable by a bright region, which provides appreciable contrast with the background. Without showing an example, it is to be understood that upon defocusing in the opposite direction along the z-axis, the cells may be identified by a dark region, as opposed to a bright region, relative to the background. In a third image, FIG. 6C, an image in which cells that are identified by the automated thresholding algorithm, and which are shown in false color. Counting the cells then becomes a straightforward automated task that can be performed using a suitably programmed computer-based system.

Operation

Figure 7:
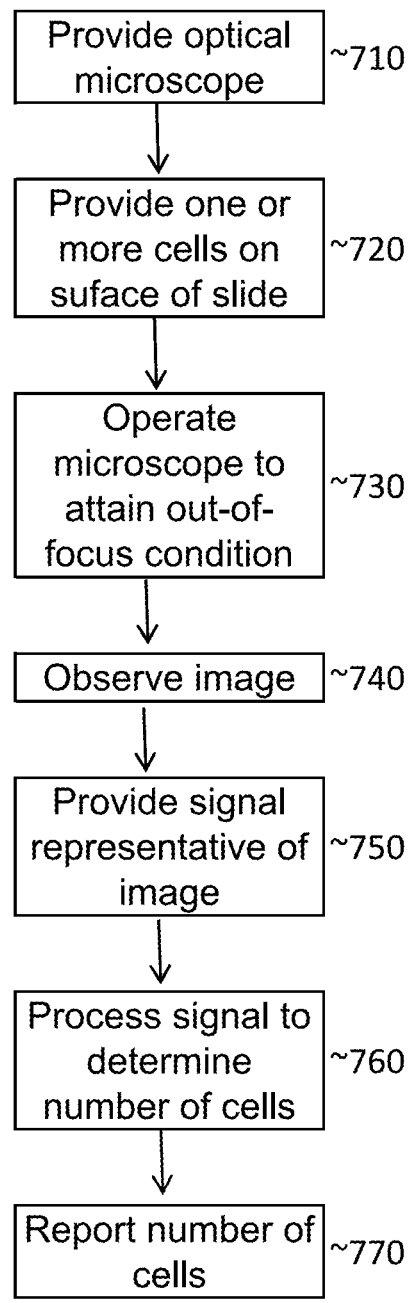
FIG. 7 is a flow diagram that illustrates the steps performed in employing the method and the automated system of the invention.

FIG. 7 is a flow diagram that illustrates the steps performed in employing the method and the automated system of the invention. An optical microscope having a sensor sensitive to optical illumination is used, as shown in step 710. The optical microscope is provided with one or more actuators (such as electrical motors) for changing the focal condition of the optical microscope, and optionally, with one or more actuators for changing one or more of lenses (such as an objective lens or an eyepiece lens) so as to change a magnification or a dimension of a field of view. A source of illumination for operating the optical microscope in bright field mode is provided. The sensor sensitive to optical illumination has an output terminal configured to provide as output a signal representative of a field of view monitored by the sensor. A sample slide having a surface is situated for observation in the optical microscope. A sample comprising at least one cell is situated on the surface of the sample slide, as shown in step 720. The sample is free of extraneous chemical substances. The optical microscope is operated in bright field mode with optical illumination so as to focus along a direction normal to the surface of the sample slide, so that the at least one cell is within the field of view of the sensor and the at least one cell is in an out of focus condition, as shown in step 730. Depending on the out of focus condition, one can observe an image having either one or more bright spots or one or more dark spots, each of which spots corresponds to a cell, as shown in step 740. The out of focus condition can be determined automatically by varying the distance between the surface of the slide and the surface of an objective lens so that the observed image varies from one of bright spots to no spots to dark spots (or the reverse sequence) while recording the relative distance between the surface of the slide and the surface of an objective lens. A distance that corresponds to either the bright spot condition or the dark spot condition can then be reproduced. The sensor provides an output signal representative of the image, as shown in step 750. One then processes the output signal representative of the image using a computer and suitable software as has been described hereinabove to compute a number of bright spots or a number of dark spots, as shown in step 760. The computer then reports the number of bright spots or the number of dark spots as the number of cells present in the sample, as shown in step 770. The report can be in the form of an image displayed in false color, or in the form of a number. The report can be recorded for later use, can be displayed to a user, or can be otherwise provided as output in any convenient format.

Figure 8:
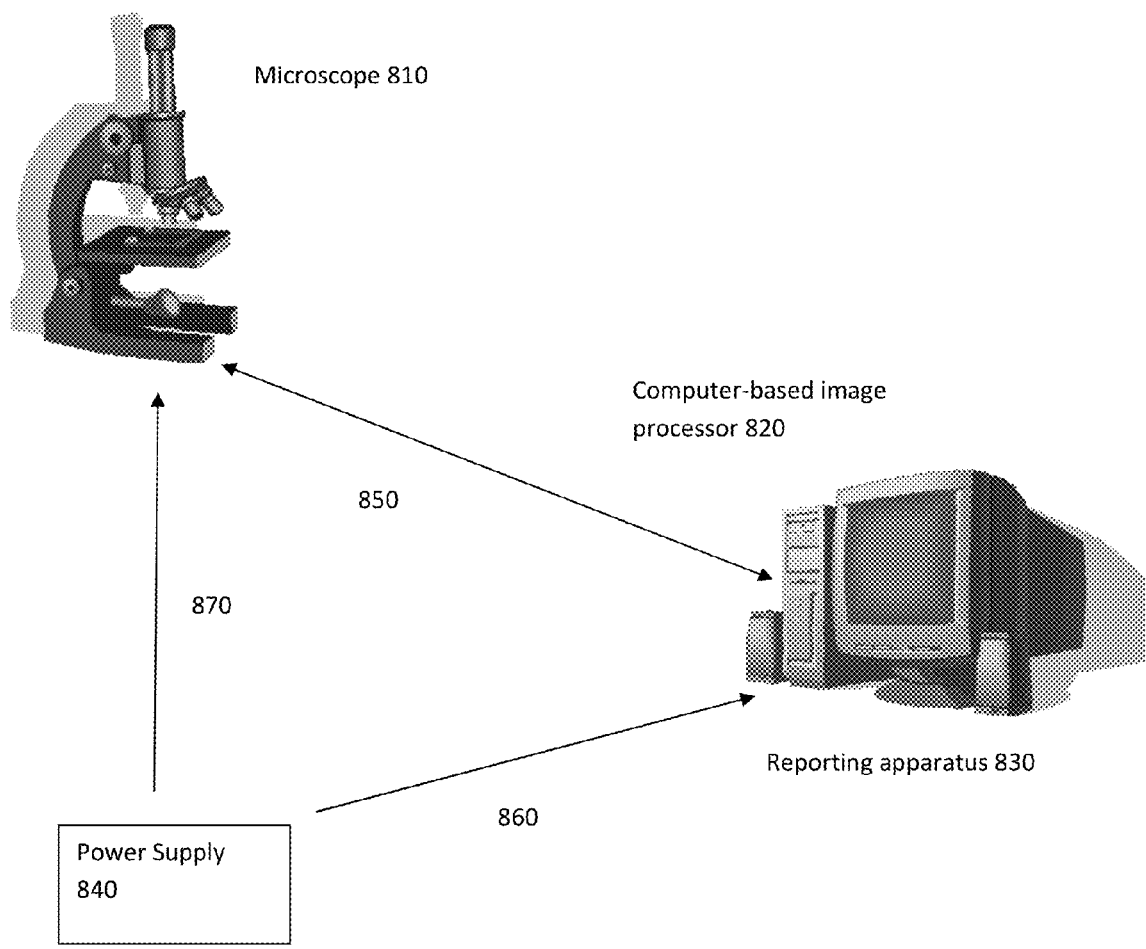
FIG. 8 is a diagram illustrating the components and connections present in an exemplary automated image processing system.

FIG. 8 is a diagram illustrating the components and connections present in an exemplary automated image processing system. In FIG. 8, a microscope 810 is connected to a computer-based image processor 820 by way of bidirectional signaling link 850. In some embodiments, the computer-based image processor 820 can be a suitably programmed personal computer. The computer-based image processor 820 is in communication with a reporting apparatus 830, such as a computer display. A power supply 840 provides power to the microscope 810 by way of link 870 and provides power to the computer-based image processor 820 and the reporting apparatus 830 by way of link 860. In some embodiments, one or more power supplies to operate the optical microscope, the computer-based image processor, and the reporting apparatus are provided.

In some embodiments, the sample does not include a staining agent, and in other embodiments the sample does not include a fluorescent agent. In some embodiments, a human operator can view the cells to be analyzed. In some instances, the optical microscope is configured to allow simultaneous mounting of a sensor and an eyepiece suitable for a human operator. In some instances, the microscope is operated to focus on one or more cells in the field of view prior to performing the cell counting method.

Framework for Cell Detection from Bright Field Image Stack

We now describe a general framework for detecting cells in an automated manner from a stack of brightfield images taken at different planes of focus. Automated analysis of brightfield images has been considered more challenging than the analysis of fluorescence labeled images, since without labeling the cells have low contrast compared to the background. The analysis framework described here relies on depth information, enabling the detection of cells in an equivalent manner to fluorescence image analysis. The framework provides a straightforward way to describe various analysis pipelines, which can be considered as realizations of the framework. We provide examples of such analysis pipelines and show that the cell detection can be efficiently done from image stacks taken with various microscopes completely without staining of cells.

Generally it has been accepted that fluorescence labeling enables more efficient automated analysis mainly due to the availability of nuclei labeling, which can be used for cell detection and subsequently the detected cells can be used as cell markers or seeds for further analysis. However, despite the benefits of fluorescence labeling, imaging cells in brightfield without any labeling has its advantages. Being free of fluorophores means that the cells do not suffer from phototoxicity, nor does photobleaching of the fluorophores affect the results. Moreover, provided that the cell detection could be done in an automated and reliable manner, the brightfield images provide the actual cell shape more accurately since the detection of the cell shape does not depend on label distribution in the cell body.

Fluorescence labeling, through the emergence of highly specific stains, is ideal for staining of specific subcellular structures, making it a valuable measurement platform in high throughput studies where cell responses are often measured through quantification of subcellular activity. However, with the development of specific stains, only a limited number of channels may be imaged simultaneously from the same sample. For example, the use of a fluorescence stain for nuclei and cell body labeling may reduce by two the use of possible subcellular stains needed to study specific processes. In such cases, techniques that enable detection of cells from brightfield images would free up fluorescence channels for other uses.

Traditionally, fully automated analysis of brightfield images has been recognized as a difficult problem, with many segmentation methods relying on manually given seeds. Spatially tight arrangement of cells is particularly challenging for the analysis, since typically cell borders are not clearly visible. We have described a method for cell boundary detection which relies on using stacks of brightfield images where the same sample has been imaged successively in different focus levels. The focus stacks, also called z-stacks, were processed by taking projections in the z-dimension. Using the projections as markers for cell areas the cell shape and boundary determination was possible with performance similar to fluorescence labeling. While being useful in determining the whole cell area, full automation of individual cell detection was hampered by the requirement of getting the seed points by the user, or by using nuclei fluorescence markers as cell seeds. The use of focus stacks, however, is not limited to cell boundary detection. A full brightfield approach for detecting individual cells is possible by combining cell seed detection and boundary detection. Here we extend and formalize the principle of the z-stack based analysis by presenting a generic framework for fully automated cell detection from bright field images. Noise, background fluctuations, debris or small particles such as dust appearing on the in-focus frame do not affect the detection.

Construction and Properties of Brightfield Focus Image Stacks

To start with, let us define a stack of brightfield images as $I_z(x, y)$, where $z \in 1, \ldots, N$ defines the frame starting from frame I1 above focus and ending in IN below focus, and x, y are the spatial pixel coordinates in a n×m image. The stack, imaged by focusing through the sample, contains frames which are completely out of focus, and some which can be said to be in focus or partially in focus. Regularly the analysis of brightfield images completely discards out-of-focus frames, thereby omitting the majority of the data in a stack. Probably the most common way to utilize the focus stack is to use some data driven heuristics for choosing the frame that is in focus, and using only it for subsequent analysis. The brightfield image stacks of cell populations have certain properties which can be utilized in the analysis. Before coming to the in-focus frame, the cells appear as bright, blurred objects (that is, they appear to be bright spots). Moving towards the optimal focus level the intensity of the cells rapidly changes into almost transparent, while the details become visible when the cells are in focus. Further, moving away from the in-focus frame the cells become blurred again, but instead of the high intensity appearance, this time the cells have low intensity (that is, they appear to be dark spots).

One of the key elements in our proposed framework is that the image stack is processed in two halves. By defining a frame Nl as the splitting frame such that the upper half (or upper group) consists of frames $I1(x, y) \ldots INl(x, y)$ and subsequently the lower half (or lower group) of frames $INl+1(x, y) \ldots IN(x, y)$. Thus, defining the frame Nl is significant to the remainder of the analysis. The frame Nl can be selected for example by choosing the frame in the middle of the stack, provided that the imaging has been done such that approximately as many frames have been taken above and below focus. Another option for selecting the frame Nl would be to use some heuristics for determining the in focus frame, such as a robust autofocus method known in the art, as described in J. M. Geusebroek, F. Cornelissen, A. W. Smeulders, and H. Geerts, "Robust autofocusing in microscopy." *Cytometry*, vol. 39, no. 1, pp. 1-9, January 2000, or in A. G. Valdecasas, D. Marshall, J. M. Becerra, and J. J. Terrero, "On the extended depth of focus algorithms for bright field microscopy." *Micron*, vol. 32, no. 6, pp. 559-569, August 2001.

Detection Based on Stack Disparity

Figure 9:
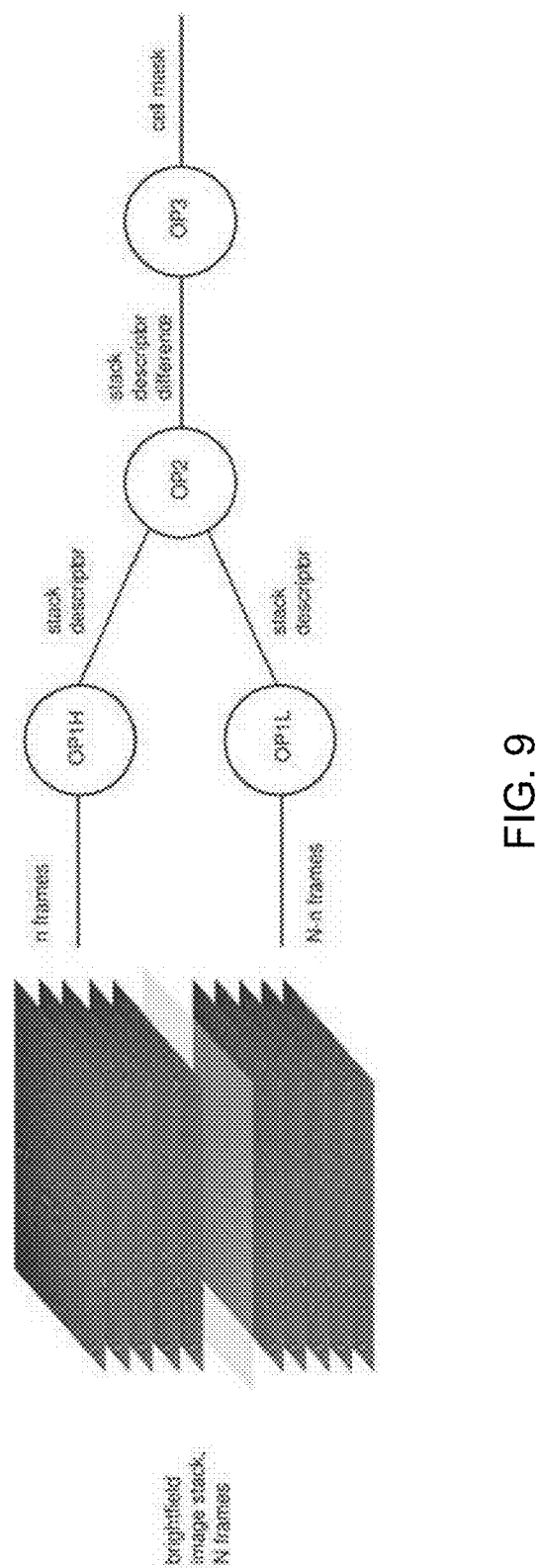
FIG. 9 is a schematic diagram that illustrates a framework for cell detection from brightfield image stack data, in which OP denotes a mathematical operation as described herein.

First, we formalize a so-called disparity based cell marker detection. The disparity refers to the different appearance of cells when considering different levels of a z-stack. The disparity in the cell appearance in different levels creates the basis for detection. Especially the property of cells having bright appearance in the above focus part and on the other hand, dark appearance below focus, enables characterizing cell locations in the images. In addition, the fact that background stays generally unchanged throughout the stack is another observation that backs the disparity-based detection. Now, let us consider the framework described in FIG. 9. By setting the operation OP1 (both OP1H and OP1L) as median in the z-direction, we create two projections based on the stack. Thus, the operation OP1H is defined as $$SH(x,y)=\text{med}\{I1(x,y), I2(x,y), \ldots, INl(x,y)\} \qquad \text{Eqn. (7)}$$

which is the pixelwise median in the z-dimension and where Nl defines the frame splitting the stack. Similarly the OP1L is defined as $$SL(x,y)=\text{med}\{INl+1(x,y), INl+2(x,y), \ldots, IN(x,y)\} \qquad \text{Eqn. (8)}$$

The output from Eqn. 7 and Eqn. 8 are the so-called stack descriptors SH and SL. Notably, all frames in the stack are considered when building the stack descriptors. By utilizing the whole z-stack, the objects appearing on different focus levels can be detected. It should be noted that the framework does not limit the operation in any way. For example, the median operation can be seen as a special case of percentile, and by choosing OP1H as the Pth percentile and OP1L as the 1-Pth percentile, another modification of the framework can be obtained. Furthermore, median filter can also be seen as a special case of the family of stack filters (see J. Astola and P. Kuosmanen, *Fundamentals of nonlinear digital filtering*, CRC Press, 1997). In another embodiment, stack filters could be applied to enable detection instead of median as has been described in J. Yoo, E. Coyle, and C. Bouman, "Dual stack filters and the modified difference of estimates approach to edge detection," *IEEE Transactions on Image Processing*, vol. 6, pp. 1634-1645, 1997.

Operation OP2 is then used for comparing the stack descriptors. Here, OP2 is defined as a pixelwise difference of the descriptors. The outcome, which is called as the stack descriptor difference, is thus defined as $$D(x,y)=SH(x,y)-SL(x,y).$$

Recalling the general properties of brightfield image stacks—background stays rather unchanged, while cells are bright in the upper half and dark in the lower half—the polarity difference can be assumed to form an image where cells are enhanced and background suppressed. As a result, detection of cells can be done by segmenting the difference image D in operation OP3. Here we use the minimum error thresholding method, described in J. Kittler and J. Illingworth, "Minimum error thresholding," *Pattern Recognition*, vol. 19, pp. 41-47, 1986, for determining the threshold value tme in an automated manner, and the initial cell detection becomes $$BW(x,y)=1 \text{ if } D(x,y)>tme, BW(x,y)=0 \text{ otherwise} \qquad \text{Eqn. (9)}$$

In principle, however, any method that is applicable in cell nuclei detection from fluorescence labeled images could also be used here as OP3.

Detection Based on Optimal Intensity Frame

Another realization of the framework is obtained when the brightness of cells in the stack prior to the in-focus level is utilized in an alternative way. This time the first operation OP1H simply picks one of the frames Ij in the stack according to the following criterion $$\text{argmax}_{z\in i\ldots Nl} \sum_{i=1}^{L} p_{iz}. \qquad \text{Eqn. (10)}$$

where z defines the frame in the stack ($z\in 1, , Nl$), $p_{iz}$, is the probability of intensity i in frame z which can be obtained from intensity histogram, L is the intensity maximum in the stack, and/is defined as the intensity corresponding to the Pth percentile (given as $P\Sigma[0, 1]$) of the intensities in the stack. The operation picks the frame which has the highest number of bright pixels belonging to the top 1-P rank in the stack intensities. Now, setting P to 0.995 gives us the frame having most of the top 0.5% pixel values, and indeed this frame shows the cells as blurred but bright objects. Unlike the disparity method, this approach uses one of the original frames for further analysis instead of creating a stack descriptor frame based on all the frames. Here we omit detailed definition of OP1L, but it can be obtained by replacing the upper half of the stack by the lower half in Eqn. 10.

After selecting the optimal intensity frame maximizing the criterion in Eqn. 10 from both stack halves as the stack descriptors, the second operation OP2 selects the frame from these two that comes from a feasible focus range (in this case, the frame should have cells visible as bright spots, thus the operation should pick the frame originating from above-focus stack). This can be done typically by assuming that the bright appearance of cells peaks in the first half, and thus from the two maxima selected by OP1 the one that has bigger value for the criterion expressed in Eqn. 10 is the correct one. Similarly as in the stack disparity method, also here many operations typical in nuclei segmentation would be applicable. For comparison, we apply the same minimum error thresholding as previously.

Detection Based on Focus Differential

The third realization of the framework relies on the same principle as the disparity-based methods—when moving from above focus to below focus, the cell areas usually turn from bright to dark spots while areas outside or near cell borders show the opposite behavior and background stays rather constant. Thus, the direction of a derivative could be used as a basis for detection. Let us define OP1 (for both OP1H and OP1L) as $$Diff(x,y) = \frac{\Delta I_z(x,y)}{\Delta z} = I_z(x,y) - I_{z-1}(x,y) \qquad \text{Eqn. (11)}$$

Detection Results

The results provide examples on how the cell detection framework can be used in typical cell image analysis cases. In more detail, we show how the framework enables cell quantification from bright field image stacks when cells are tightly packed and how the cell detection can be used as a basis of cell tracking using only bright field images.

Cell Detection from Image Stacks

The typical analysis pipeline for fluorescence labeled cell population images starts by cell detection from channel where nuclei have been labeled (sometimes referred to as primary object detection), and then proceeds to cell border detection from another fluorescent channel (secondary object detection). Cell outline detection is possible also from brightfield images, but the lack of cell nuclei labeling poses a challenge when cells are closely located. Here we demonstrate how the framework can be used as a replacement for nuclei labeling. Together with the projection-based cell outline detection the method provides a solution to whole cell image analysis equivalent to fluorescence labeling.

We tested the cell detection from altogether 12 brightfield image stacks of cells imaged at 40× magnification. The detection accuracy was determined by observing the correctly detected cells (true positive, tp), false detections (false positive, fp), and missing detections (false negative, fn). Using these figures, the commonly used metrics describing the detection accuracy, namely precision p=tp/(tp+fp), recall r=tp/(tp+fn) and F-score=2×precision×recall=(precision+recall), were calculated. The results are given in Table 3.

TABLE 3

Cell detection results from brightfield image stacks.

| Parameter | tp | fp | fn | p | R | F |
|---|---|---|---|---|---|---|
| Value | 178 | 5 | 10 | 0.9793 | 0.9553 | 0.9671 |

The Framework Enables Live Cell Monitoring

Here we provide an example of macrophage cell tracking by using the proposed framework. We used a set of 193 image stacks, imaged in 5 minute intervals for a time period of 16 hours for testing. Cell detection was done by using the proposed framework with the operation described in DETECTION BASED ON FOCUS DIFFERENTIAL, and the nuclei tracking method of X. Chen, X. Zhou, and S. Wong, "Automated segmentation, classification, and tracking of cancer cell nuclei in time-lapse microscopy," *IEEE Transactions on Biomedical Engineering*, vol. 53, no. 4, pp. 762-766, 2006 was used for tracking the cells. The tracking result is shown in FIG. 18.

The proposed framework can be customized into various analysis pipelines by modifying the operations used for processing stacks. In particular, the methods do not require any manual initializations, seed points or labeling, and they can be considered as a potential replacement for using cell nuclei labeling as a cell marker. In fact, the replacement of nuclei labeling was demonstrated by using a standard fluorescence analysis software, A. Carpenter, T. Jones, M. Lamprecht, C. Clarke, I. Kang, O. Friman, D. Guertin, J. Chang, R. Lindquist, J. Moffat, P. Golland, and D. Sabatini, "CellProfiler: image analysis software for identifying and quantifying cell phenotypes." *Genome Biol*, vol. 7, no. 10, p. R100, 2006, for cell mask segmentation from a processed stack. The framework converts bright field image stacks such that they share typical properties of fluorescence labeled images. The consequence of this is that the vast variety of analysis methods developed for fluorescence microscopy becomes applicable for bright field images whenever proper image stacks are available. It should be also noted that the use of the framework does not exclude the possibility to use fluorescence labeling for providing further insight into detailed cell structure and functions. In fact the framework enables the use of one to two additional fluorescent channels for labeling specific cell compartments by replacing channels required for cell nuclei and body labeling.

Definitions

Recording the results from an imaging operation or image acquisition, such as for example, recording results at a particular focal condition, is understood to mean and is defined herein as writing output data to a storage element, to a machine-readable storage medium, or to a storage device.

Machine-readable storage media that can be used in the invention include electronic, magnetic and/or optical storage media, such as magnetic floppy disks and hard disks; a DVD drive, a CD drive that in some embodiments can employ DVD disks, any of CD-ROM disks (i.e., read-only optical storage disks), CD-R disks (i.e., write-once, read-many optical storage disks), and CD-RW disks (i.e., rewriteable optical storage disks); and electronic storage media, such as RAM, ROM, EPROM, Compact Flash cards, PCMCIA cards, or alternatively SD or SDIO memory; and the electronic components (e.g., floppy disk drive, DVD drive, CD/CD-R/CD-RW drive, or Compact Flash/PCMCIA/SD adapter) that accommodate and read from and/or write to the storage media. As is known to those of skill in the machine-readable storage media arts, new media and formats for data storage are continually being devised, and any convenient, commercially available storage medium and corresponding read/write device that may become available in the future is likely to be appropriate for use, especially if it provides any of a greater storage capacity, a higher access speed, a smaller size, and a lower cost per bit of stored information. Well known older machine-readable media are also available for use under certain conditions, such as punched paper tape or cards, magnetic recording on tape or wire, optical or magnetic reading of printed characters (e.g., OCR and magnetically encoded symbols) and machine-readable symbols such as one and two dimensional bar codes. Recording image data for later use (e.g., writing an image to memory or to digital memory) can be performed to enable the use of the recorded information as output, as data for display to a user, or as data to be made available for later use. Such digital memory elements or chips can be standalone memory devices, or can be incorporated within a device of interest. "Writing output data" or "writing an image to memory" is defined herein as including writing transformed data to registers within a microcomputer.

"Microcomputer" is defined herein as synonymous with microprocessor, microcontroller, and digital signal processor ("DSP"). It is understood that memory used by the microcomputer, including for example an imaging or image processing algorithm coded as "firmware" can reside in memory physically inside of a microcomputer chip or in memory external to the microcomputer or in a combination of internal and external memory. Similarly, analog signals can be digitized by a standalone analog to digital converter ("ADC") or one or more ADCs or multiplexed ADC channels can reside within a microcomputer package. It is also understood that field programmable array ("FPGA") chips or application specific integrated circuits ("ASIC") chips can perform microcomputer functions, either in hardware logic, software emulation of a microcomputer, or by a combination of the two. Apparatus having any of the inventive features described herein can operate entirely on one microcomputer or can include more than one microcomputer.

General purpose programmable computers useful for controlling instrumentation, recording signals and analyzing signals or data according to the present description can be any of a personal computer (PC), a microprocessor based computer, a portable computer, or other type of processing device. The general purpose programmable computer typically comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of UNIX, or of Linux. Computational results obtained in the operation of the general purpose computer can be stored for later use, and/or can be displayed to a user. At the very least, each microprocessor-based general purpose computer has registers that store the results of each computational step within the microprocessor, which results are then commonly stored in cache memory for later use.

Many functions of electrical and electronic apparatus can be implemented in hardware (for example, hard-wired logic), in software (for example, logic encoded in a program operating on a general purpose processor), and in firmware (for example, logic encoded in a non-volatile memory that is invoked for operation on a processor as required). The present invention contemplates the substitution of one implementation of hardware, firmware and software for another implementation of the equivalent functionality using a different one of hardware, firmware and software. To the extent that an implementation can be represented mathematically by a transfer function, that is, a specified response is generated at an output terminal for a specific excitation applied to an input terminal of a "black box" exhibiting the transfer function, any implementation of the transfer function, including any combination of hardware, firmware and software implementations of portions or segments of the transfer function, is contemplated herein, so long as at least some of the implementation is performed in hardware.

THEORETICAL DISCUSSION

Although the theoretical description given herein is thought to be correct, the operation of the devices described and claimed herein does not depend upon the accuracy or validity of the theoretical description. That is, later theoretical developments that may explain the observed results on a basis different from the theory presented herein will not detract from the inventions described herein.

Any patent, patent application, or publication identified in the specification is hereby incorporated by reference herein in its entirety. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

While the present invention has been particularly shown and described with reference to the preferred mode as illustrated in the drawing, it will be understood by one skilled in the art that various changes in detail may be affected therein without departing from the spirit and scope of the invention as defined by the claims.

What is claimed is:

1. A method of automatically identifying the number of cells present in a sample, comprising the steps of:
providing an optically transparent supporting surface, said optically transparent supporting surface situated for observation in an optical microscope having a sensor sensitive to optical illumination, said sensor having an output terminal configured to provide as output a signal representative of a field of view monitored by said sensor;
providing a sample comprising at least one cell situated on said optically transparent supporting surface;
deliberately operating said optical microscope in bright field mode with optical illumination so as to focus at one or more different focal planes situated along a direction normal to said optically transparent supporting surface, so that said at least one cell is within said field of view of said sensor;
observing with said sensor an image selected from the group of images consisting of an image having one or more bright spots and an image having one or more dark spots, said image having one or more bright spots and said image having one or more dark spots generated even when said sample is free of a label, said image corresponding to an out-of-focus condition;
providing from said output terminal of said sensor an output signal representative of said image;
processing said output signal representative of said image to compute a number of bright spots or a number of dark spots; and
reporting said number of bright spots or said number of dark spots as the number of cells present in said sample.

2. The method of automatically identifying the number of cells present in a sample of claim 1, wherein said label is a staining agent.

3. The method of automatically identifying the number of cells present in a sample of claim 1, wherein said label is a fluorescent agent.

4. The method of automatically identifying the number of cells present in a sample of claim 1, further comprising the step of having a human operator view an image observed by said sensor.

5. The method of automatically identifying the number of cells present in a sample of claim 1, wherein said step of processing said output signal representative of said image is performed in a computer-based analyzer.

6. The method of automatically identifying the number of cells present in a sample of claim 5, wherein said computer based-analyzer provides a synthetic image of said sample comprising at least one cell, said synthetic image including an outline of said at least one cell in false color.

7. The method of automatically identifying the number of cells present in a sample of claim 1, further comprising the step of focusing on said at least one cell, said step of focusing on said at least one cell being performed prior to said step of observing with said sensor an image selected from the group of images consisting of an image having one or more bright spots and an image having one or more dark spots.

8. An automated image processing system, comprising:
an optical microscope having a sensor sensitive to optical illumination, said sensor having an output terminal configured to provide as output a signal representative of a field of view monitored by said sensor, said optical microscope configured to allow operation of said optical microscope in bright field mode with optical illumination and configured to allow said optical microscope to change focus along a direction normal to an optically transparent supporting surface situated for observation in said optical microscope so as deliberately to attain at least one image along said direction normal to said optically transparent supporting surface of a sample situated within said field of view of said optical microscope;
a computer-based image processor configured to receive said output signal representative of a field of view monitored by said sensor from said sensor, said image processor configured to identify one or more images out of said at least one image, said image processor configured to analyze said at least one image to deduce a property of said sample from said one or more images, said one or more images out of said at least one image is a selected one of an image having one or more bright spots and an image having one or more dark spots generated when said optical microscope is in an out-of-focus condition and sample is free of a label; and a reporting apparatus in communication with said computer-based image processor, said reporting apparatus configured to provide a report of said property of said sample.

9. The automated image processing system of claim 8, wherein:
said image processor is configured to compute a number of bright spots or a number of dark spots in said image; and
said property reported by said reporting apparatus is said number of bright spots or said number of dark spots, so that said property reported is a number of cells present in a sample situated on a portion of said optically transparent supporting surface that is situated within said field of view of said optical microscope.

10. The automated image processing system of claim 8, further comprising:
an actuator configured to change a focal condition of said optical microscope.

11. The automated image processing system of claim 10, further comprising:
a computer-based control apparatus configured to control said focal condition of said optical microscope by driving said actuator.

12. The automated image processing system of claim 11, wherein said computer-based control apparatus configured to control said focal condition of the optical microscope is configured to operate to focus at one or more different focal planes situated along said normal to said optically transparent supporting surface on one or more cells in the field of view.

13. The automated image processing system of claim 8, further comprising:
an actuator configured to change a lens so as to change a magnification or a dimension of a field of view of said optical microscope.

14. The automated image processing system of claim 8, wherein said reporting apparatus provides a synthetic image.

15. The automated image processing system of claim 14, wherein said synthetic image includes false color.

16. The automated image processing system of claim 8, wherein said reporting apparatus provides a report that is recorded for later use.

17. The automated image processing system of claim 8, wherein said reporting apparatus provides a report that is displayed to a user.

18. The automated image processing system of claim 8, wherein said optical microscope is configured to allow simultaneous mounting of said sensor and an eyepiece suitable for a human operator.

19. The automated image processing system of claim 8, further comprising:
one or more power supplies to operate said optical microscope, said computer-based image processor, and said reporting apparatus.

20. The automated image processing system of claim 8, wherein:
said at least one image is selected from a bright field z-stack of images along a z-dimension;

said image processor is configured to compute a variation with respect to said z-dimension of said intensity values within said x,y plane between a first image and a second image of said bright field z-stack, to construct a two-dimensional projection image of increased contrast, and to deduce from said two-dimensional projection image of increased contrast a feature of at least one cell of said sample; and said reporting apparatus is configured to report said feature of said at least one cell present in said sample.

21. The automated image processing system of claim 8, wherein said property is a border of said at least one cell.

22. The automated image processing system of claim 8, wherein said system is configured to spatially distinguish at least one cell from another cell within said sample.

23. A method of automatically identifying a feature of a cell present in a sample, comprising the steps of:
providing an optically transparent supporting surface, said optically transparent supporting surface situated for observation in an optical microscope having a sensor sensitive to optical illumination, said sensor having an output terminal configured to provide as output a signal representative of a field of view monitored by said sensor;
providing a sample comprising at least one cell situated on said optically transparent supporting surface;
deliberately operating said optical microscope in bright field mode with optical illumination so as to focus at one or more different focal planes situated along a direction normal to said optically transparent supporting surface to form a bright field z-stack of images along a z-dimension, so that said at least one cell is within said field of view of said sensor;
observing with said sensor a plurality of images selected from said bright field z-stack;
providing from said output terminal of said sensor an output signal representative of said plurality of images;
processing for at least two of said plurality of images said output signal representative of said plurality of images to obtain intensity values of pixels within an x,y plane, one of said at least two of said plurality of images being in an out-of-focus condition and sample is free of a label;
measuring a variation with respect to said z-dimension of said intensity values within said x,y plane between a first image and a second image of said at least two of said plurality of images;
constructing a two-dimensional projection image of increased contrast;
deducing from said two-dimensional projection image of increased contrast a feature of said at least one cell; and
reporting said feature of said at least one cell present in said sample.

24. The method of automatically identifying a feature of a cell present in a sample of claim 23, wherein said feature is an observable property of said at least one cell.

25. The method of automatically identifying a feature of a cell present in a sample of claim 24, wherein said observable property is a border of said at least one cell.

26. The method of automatically identifying a feature of a cell present in a sample of claim 23, wherein said at least one cell is spatially distinguished from another cell within said sample.

27. The method of automatically identifying the number of cells present in a sample of claim 1, wherein, when said optical microscope is operated in a deliberately out-of-focus condition, either all of the cells in an image appear to have a bright spot or all of the cells in an image appear to have a dark spot that can be used to report the number of cells in the sample.

* * * * *